(12) United States Patent
Kinnersley et al.

(10) Patent No.: US 6,534,446 B1
(45) Date of Patent: *Mar. 18, 2003

(54) METHOD TO MITIGATE PLANT STRESS

(75) Inventors: Alan M. Kinnersley, East Lansing, MI (US); Brooks A. Bauer, Escalon, CA (US); Kristine L. Crabtree, Okemos, MI (US); Cheng-Yuh Kinnersley, East Lansing, MI (US); John L. McIntyre, Alto, MI (US); Sarah E. Daniels, Lansing, MI (US)

(73) Assignee: Emerald BioAgriculture Corporation, Lansing, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/166,434

(22) Filed: Oct. 5, 1998

Related U.S. Application Data

(63) Continuation-in-part of application No. 08/744,593, filed on Nov. 6, 1996, now Pat. No. 5,840,656, which is a continuation-in-part of application No. 08/511,498, filed on Aug. 4, 1995, now abandoned, which is a continuation of application No. 08/500,391, filed on Jul. 10, 1995, now Pat. No. 5,604,177, which is a continuation of application No. 08/200,218, filed on Feb. 23, 1994, now Pat. No. 5,439,873.

(51) Int. Cl.[7] .......................... A01N 37/04; A01N 37/44
(52) U.S. Cl. ...................... 504/147; 504/158; 504/326
(58) Field of Search ................................. 504/158, 326

(56) References Cited

U.S. PATENT DOCUMENTS

| | | | |
|---|---|---|---|
| 4,491,464 A | 1/1985 | Ashmead et al. | 71/11 |
| 4,870,172 A | 9/1989 | Okami et al. | 540/460 |
| 4,908,353 A | 3/1990 | Yamamoto et al. | 514/19 |
| 4,950,606 A | 8/1990 | Stirling et al. | 435/280 |
| 4,957,757 A | 9/1990 | Law et al. | 426/281 |
| 5,439,873 A | 8/1995 | Kinnersley | 504/158 |
| 5,593,947 A | 1/1997 | Kinnersley et al. | 504/283 |
| 5,597,400 A | 1/1997 | Nonomura et al. | 71/28 |
| 5,604,177 A | 2/1997 | Kinnersley et al. | 504/147 |
| 5,840,656 A | 11/1998 | Kinnersley et al. | 504/115 |
| 5,972,840 A | 10/1999 | Mottram | 504/244 |

OTHER PUBLICATIONS

M. Santos, I. Claparols & J.M. Torne; "Effect of Exogenous Arginine, Ornithine, Methionine and GABA on Maize (*Zea Mays* L.) Embryogenesis and Polyamine Content," J. Plant Physiol., vol. 142, 1993, pp. 74–80, XP002075993.

Derwent Publications Ltd., AN 81–63554D, XP002075994 and JP 56032961B (Ajinomoto KK) (Abstract).

Chemical Abstracts 74:95454r (1971).

CABA Abstract 73:30077 (1973).

WPIDS Abstract 85–084635 (1985).

Chemical Abstract 93:235305n (1980).

Chemical Abstract 116:20002u (1991).

Chemical Abstract 99:36050z (1983).

SOLU–SPRAY Pamphlet by: Leffingwell Chemical Company, 1987.

"β–Aminobutyric Acid Induces the Accumulation of Pathogenesis–Related Proteins in Tomato (*Lycopersicon esculentum* L.) Plants and Resistance to Late Blight Infection caused by *Phytophthora infestants*," Cohen, Yigal; Niderman, Tierry; Mosinger, Egon; and Fluhr, Robert. *Plant Physiol.* 104:59–66, 1994.

"The Production and Efflux of 4–Aminobutyrate in Isolated Mesophyll Cells[1]," Induk Chung, Alan W. Brown & Barry J. Shelp. *Plant Physiol.* 99:659–664, 1992.

"Comptes Rendus—Des Seances—De L'Academie Des Sciences; Physiologie Vegetale." *C.R. Acad.Sc.Paris*, t.271, Series D, pp2316–2319 (1970).

"Metabolism, Enzymology & Possible Roles of 4–Aminobutyrate in Higher Plants" (Review Article No. 51); V. Satya Narayan and P.M. Nair. *Phytochemistry*, 29:367–375, 1990.

"The Metabolism and Functions of γ–Aminobutyric Acid," Alan W. Brown and Barry J. Shelp, *Plant Physiol.* 115:1–5, 1997.

"Nitrogen Metabolism in Plant Cell Suspension Cultures," Josef Behrend and Richard I. Mateles. *Plant Physiol.* 56:584–589, 1975.

Anonymous. Gama–AminoButyric Acid. *The Merck Index*, 11th edition, 1989, p. 435, entry 441, see entire entry.

*Primary Examiner*—S. Mark Clardy
(74) *Attorney, Agent, or Firm*—Woodard, Emhardt, Naughton, Moriarty & McNett LLP

(57) ABSTRACT

The present invention provides methods for mitigating the effects of plant stress. Plant stress mitigating compounds and compositions comprising gamma aminobutyric acid and glutamic acid are also described.

67 Claims, 2 Drawing Sheets

CAS = Casein at 1,000 ppm
GABA & GLU = Gamma aminobutyric acid and Glutamic acid at 10 mM.
FERT = Fertilizer SoluSpray 20-20-20

METHOD TO MITIGATE PLANT STRESS

This application is a continuation-in-part of U.S. patent application Ser. No. 08/744,593, now U.S. Pat. No. 5,840, 656, filed Nov. 6, 1996, which is a continuation-in-part of U.S. patent application Ser. No. 08/511,498 (abandoned), filed Aug. 4, 1995, which is a continuation of U.S. patent application Ser. No. 08/500,391, filed Jul. 10, 1995, now U.S. Pat. No. 5,604,177, which is a continuation of U.S. patent application Ser. No. 08/200,218, filed Feb. 23, 1994, now U.S. Pat. No. 5,439,873.

BACKGROUND OF THE INVENTION

The present invention relates generally to methods for mitigating plant stress.

Biological stress has been defined as "any change in environmental conditions that might reduce or adversely change a plant's growth or development" (J. Levitt, 1972, *Responses of Plants to Environment Stresses*, Academic Press, Inc., New York and London). Adverse environmental conditions such as water deprivation, pathogen attack, salinity and unfavorable growing temperatures are common stresses that limit agriculture yields. For example, it has been estimated that the world rice production would decrease 50% if the world mean temperature dropped by only 1.0° C. (F. B. Salisbury & C. W. Ross, *Stress Physiology in Plant Physiology*, 1985, published by Wadsworth Inc.). Moreover, a comparison of average and record yields of eight major crops showed that average yields were only one-third to one-seventh of record yields (Boyer, Science, 1982, 218:443–448). More than 70% of the loss of potential yields was attributed to unfavorable growing conditions caused by factors such as weeds, disease, soils, climate, etc. (Id.). Unlike animals, which are able to move into less stressful environments, plants rely on chemical defenses to respond to stress. When plants are exposed to unfavorable high growing temperatures, normal protein synthesis is reduced and rapid synthesis of heat shock proteins commences (J. L. Key and Y. M. Chem 1981, *Proc. National Academy of Science* 78:3526–3530). Similarly, low temperature acclimation in plants is associated with the synthesis of specific extremely hydrophilic proteins which act as cryoprotectants, much like anti-freeze (J. G. Boothe et al., 1997, *Plant Physiol* 113:367–376). In response to invasion of plant tissues by pathogens such as insects or fungi, stress induced lignin deposition occurs to seal off the site of wounding (R. A. Dixon and N. L. Pawa, 1995, Plant Cell, 7:1085–1097). Many plants respond to drought and salinity stress by accumulating high levels of protein, which is believed to protect plant tissues from osmotic stress (G. R. Stervant, et al., 1976, *Plant* 120, 279–289).

Thus, it can be seen that plants have developed specific patterns of stress mediated metabolism in response to various environmental and biological challenges. Efforts to mitigate the effects of plant stress have included complex methodologies that are both time consuming and expensive. For example, in order to inhibit pathogenic conditions of plants, recombinant DNA technology has been used to incorporate genes into the plant genome that encode polypeptide and complementary oligonucleotide inhibitors. In order to mitigate the effects of different forms of stress, it is usually necessary to incorporate other genes into the plant's genome that will be effective in eliminating the particular stress involved. More over, prior to the present invention, most methods to mitigate stresses have been directed at specific stresses. For example, a method to protect a plant from a specific fungal infection would not be expected to protect against all fungal diseases. It would certainly not be expected to protect plants from heat or cold stress. In contrast, the present invention provides a general method for protecting plants from diverse environmental and biological stresses. A simple, safe and cost-effective method to mitigate a wide variety of plant stress is needed. The present invention addresses this need.

SUMMARY OF THE INVENTION

The present invention relates to a plant stress mitigating compound and a composition. In one aspect of the invention, a plant stress mitigating compound including gamma aminobutyric acid is provided. In another aspect of the invention, the plant stress mitigating composition including gamma aminobutyric acid and glutamic acid is provided. The composition may further include a source of proteinaceous amino acids as well as a salt of calcium.

In yet another aspect of the invention, the plant stress mitigating composition including gamma aminobutyric acid and a source of proteinaceous amino acids is provided. In a further embodiment of the invention, a plant stress mitigating composition including glutamic acid and a source of proteinaceous amino acids is provided.

In a further aspect of the invention, the compound or compositions of the present invention may be combined with a pesticide to form a synergistic composition effective in increasing the level of control of plant pathogens.

The present invention also relates to a method of mitigating the effects of plant stress. The method of mitigating the effects of plant stress includes treating the plant with a compound including gamma aminobutyric acid.

In another embodiment of the invention, a method of mitigating the effects of plant stress including treating the plant with a composition that includes gamma aminobutyric acid and glutamic acid is provided. In other embodiments of the invention, the composition may further include a source of proteinaceous amino acids and a calcium salt.

In a further embodiment of the invention, a method of mitigating the effects of plant stress including detecting the presence of stress in a plant, and treating the plant with a compound or composition as described above is provided.

In yet a further embodiment of the invention, a method of preventing plant stress or mitigating the effects of plant stress including treating the plant with the compound or composition of the present invention prior to the occurrence of plant stress is provided. The method includes initially predicting when a stressful condition will arrive prior to treating the plant.

It is an object of the invention to provide a compound effective in mitigating plant stress including gamma aminobutyric acid.

It is a further object of the invention to provide a plant stress mitigating composition including gamma aminobutyric acid and glutamic acid and including, optionally, a source of proteinaceous amino acids and a calcium salt.

It is a further object of the invention to provide a method of mitigating the effects of plant stress including treating the plant with gamma aminobutyric acid, either alone or in combination with glutamic acid and either a source of proteinaceous amino acids, a salt of calcium, or a mixture thereof.

It is a further object of the invention to provide a method of mitigating the effects of plant stress including detecting the presence of stress in a plant, and treating the plant with gamma aminobutyric acid alone or in combination with glutamic acid and either a source of proteinaceous amino acids or a salt of calcium.

It is yet a further object of the invention to provide a method of preventing plant stress including treating the plant with gamma aminobutyric acid, gamma aminobutyric acid and a source of proteinaceous amino acids, or gamma aminobutyric acid, glutamic acid and a source of proteinaceous amino acids and, optionally, with a calcium salt prior to the occurrence of plant stress.

These and other objects and advantages of the invention will be apparent from the following description.

DESCRIPTION OF THE PREFERRED EMBODIMENT

Figure 1:
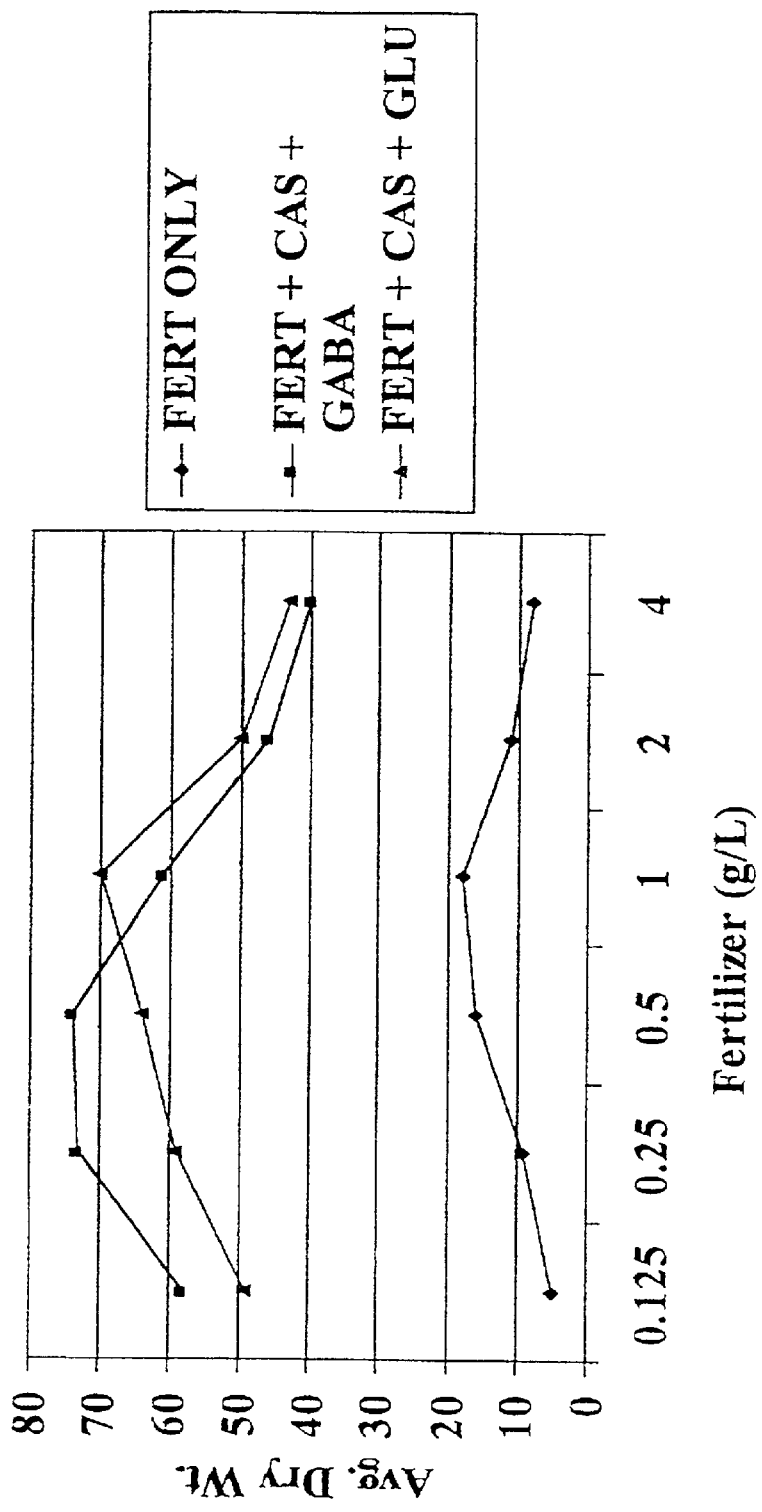
FIG. 1 is a graph of average dry weight versus concentration of fertilizer alone or in combination with casein hydrolysate and either gamma aminobutyric acid or glutamic acid. Plants were treated with fertilizer soluspray 20-20-20 alone (FERT), or in combination with either 1,000 ppm casein (CAS) and 10 mM gamma aminobutyric acid (GABA) or 1,000 ppm casein (CAS) and 10 mM glutamic acid (GLU).

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the described invention, and such further applications of the principles of the invention as illustrated therein being contemplated as would normally occur to one skilled in the art to which the invention relates.

The present invention provides compounds effective in mitigating plant stress comprising gamma aminobutyric acid. Plant stress mitigating compositions comprising gamma aminobutyric acid and glutamic acid are also described, and optionally further including, a source of proteinaceous amino acids. Moreover, compositions comprising a source of proteinaceous amino acids in combination with either glutamic acid or gamma aminobutyric acid are also described. The compounds and compositions of the present invention may optionally include a calcium salt. Additionally, methods of mitigating plant stress and methods of preventing plant stress utilizing the compounds and compositions of the present invention are also described.

In one aspect of the invention, a compound effective in mitigating plant stress is provided. Gamma aminobutyric acid may be obtained commercially, synthesized by methods known in the art or derived from fermentation as known in the art. Gamma aminobutyric acid is preferably obtained commercially or synthesized.

Gamma aminobutyric acid is typically present in an amount effective to mitigate plant stress. Concentrations of gamma aminobutyric acid and the amount of gamma aminobutyric acid of the present invention sufficient to mitigate plant stress will be dependent on the nature and degree of the stress and the type of plant and will be readily apparent to one skilled in the art. For example, mitigation of plant stress is typically observed by treating a plant with the plant stress mitigating compound or compositions of the present invention and observing either increases in dry weight of the plant, increases in the number of germinated seeds, or, in the case of stress due to infection by pathogens, discoloration or lesion depth compared to untreated plants. Preferable concentrations of gamma aminobutyric acid include about 1 ppm to about 24,000 ppm [about 0.013 oz/acre (oz/A) to about 20 lbs/A] [about 0.93 g/hectare (g/ha) to about 22 kg/ha], about 1 ppm to about 12,000 ppm (about 0.013 oz/A to about 10 lbs/A) (about 0.93 g/ha to about 11 kg/ha), about 1 ppm to about 7,500 ppm (about 0.013 oz/A to about 6.3 lbs/A) (about 0.93 g/ha to about 7.1 kg/ha) and about 1 ppm to about 5,000 ppm (about 0.013 oz/A to about 4.2 lbs/A) (about 0.93 g/ha to about 4.8 kg/ha). However, concentrations of gamma aminobutyric acid of from about 1 ppm to about 2,500 ppm (about 0.013 oz/A to about 2.1 lbs/A) (about 0.93 g/ha to about 2.4 kg/ha) are typically employed, with about 150–600 ppm (about ⅛ lb/A to about ½ lb/A) (about 0.14 kg/ha to about 0.56 kg/ha) being most frequently employed.

In another embodiment of the present invention, a plant stress mitigating composition includes gamma aminobutyric acid and glutamic acid. The composition may further include a source of proteinaceous amino acids.

Typical sources of proteinaceous amino acids which may be used in the invention are described in *Trader's Guide to Fermentation Media Formulation* 2d Ed., D. W. Zabriskie, et al., Traders Protein, Memphis, Tenn., 1980. Protein hydrolysates and yeast extracts are preferred sources of proteinaceous amino acids. Other sources of proteinaceous amino acids include blood hydrolysates, dairy and meat hydrolysates, and various vegetable protein hydrolysates such as those derived from soybeans, corn, and corn steep liquor. Preferred protein hydrolysates include casein hydrolysate and yeast extracts. The protein hydrolysate may be produced by enzymatically digesting the appropriate protein or by treating the protein with acid to form acid hydrolysis products. The yeast extract may be obtained commercially or may be obtained by methods known to those skilled in the art.

The concentration and amount of the plant stress mitigating composition sufficient to mitigate plant stress will be dependent on the factors outlined above. However, plant stress mitigating compositions comprising gamma aminobutyric acid, glutamic acid and a source of proteinaceous amino acids typically are comprised of a 1:1:1 composition of the components. A 1:1:1 composition as defined herein is a composition having equal weights of the individual components or equal volumes of solutions containing a single component provided the solutions are at the same concentration. The concentration of each component in the 1:1:1 composition ranges from about 1 ppm to about 24,000 ppm (0.013 oz/A to about 20 lbs/A) (about 0.93 g/ha to about 22 kg/ha). However, the concentration of each component in the 1:1:1 composition is typically in the range from about 1 ppm to about 5,000 ppm (about 0.013 oz/A to about 4.2 lbs/A) (about 0.93 g/ha to about 4.8 kg/ha). Further preferable concentrations of each component in the 1:1:1 composition include about 1 ppm to about 12,000 ppm (about 0.013 oz/A to about 10 lbs/A) (about 0.93 g/ha to about 11 kg/ha) and about 1 ppm to about 7,500 ppm (0.013 oz/A to about 6.3 lbs/A) (about 0.93 g/ha to about 7.1 kg/ha). Further preferable concentrations of glutamic acid include about 1 ppm to about 8,000 ppm (about 0.013 oz/A to about 6.7 lbs/A) (about 0.93 g/ha to about 7.5 kg/ha), whereas further preferable concentrations of the source of proteinaceous amino acids include about 19 ppm to about 6,000 ppm (¼ oz/A to about 5 lbs/A) (about 17.7 g/ha to about 5.6 kg/ha).

In other aspects of the invention, a plant stress mitigating composition including a source of proteinaceous amino acids combined with either glutamic acid or gamma aminobutyric acid are provided.

The concentration and amount of the composition including a source of proteinaceous amino acids and either glutamic acid or gamma aminobutyric acid sufficient to mitigate plant stress will vary as described above. However, the composition that includes a source of proteinaceous amino acids and glutamic acid typically contain about 2.5 ppm to about 24,000 ppm (0.03 oz/A to about 20 lbs/A) (2.33 g/ha to about 22 kg/ha), and preferably, about 19 ppm to about 6,000 ppm (¼ oz/A to about 5 lbs/A) (about 17.7 g/ha to about 5.6 kg/ha) of the source of proteinaceous amino acids, and about 1 ppm to about 8,000 ppm (0.013 oz/A to about 6.7 lbs/A) (about 0.93 g/ha to about 7.5 kg/ha), and preferably, about 1 ppm to about 7,500 ppm (0.013 oz/A to about 6.3 lbs/A) (about 0.93 g/ha to about 7.1 kg/ha) of glutamic acid.

Compositions including gamma aminobutyric acid and a source of proteinaceous amino acids typically include similar concentrations of the source of proteinaceous amino acids as described for the compositions including glutamic acid and the source of proteinaceous amino acids above. Concentrations of gamma aminobutyric acid include about 1 ppm to about 24,000 ppm (0.013 oz/A to about 20 lbs/A) (about 0.93 g/ha to about 22 kg/ha), about 1 ppm to about 12,000 ppm (0.013 oz/A to about 10 lbs/A) (about 0.93 g/ha to about 11 kg/ha), about 1 ppm to about 5,000 ppm (about 0.013 oz/A to about 4.2 lbs/A) (about 0.93 g/ha to about 4.9 kg/ha), about 1 ppm to about 2,500 ppm (about 0.013 oz/A to about 2.1 lbs/A) (about 0.93 g/ha to about 2.4 kg/ha), but most preferably, about 1 ppm to about 7,500 ppm (about 0.013 oz/A to about 6.3 lbs/A) (about 0.93 g/ha to about 7.1 kg/ha).

The plant stress mitigating compound and compositions mentioned above are preferably combined with a calcium salt, including calcium chloride, calcium phosphate, calcium sulfate and calcium nitrate. Calcium nitrate is the preferred salt. For example, gamma aminobutyric acid is preferably combined with calcium nitrate, as is the composition comprising gamma aminobutyric acid, glutamic acid and a source of proteinaceous amino acids, the composition comprising gamma aminobutyric acid and glutamic acid, as well as the compositions comprising a source of proteinaceous amino acids combined with either glutamic acid or gamma aminobutyric acid.

The plant stress mitigating compound and compositions mentioned above may be combined with a carrier medium as is known in the art. For example, the compound and compositions may be combined with water, including distilled and tap water, or a fertilizer solution. One skilled in the art would be familiar with the various fertilizer solutions which may be employed. The compound and compositions are preferably combined with tap water or tap water with additional minerals.

The plant stress mitigating compound and compositions of the present invention may contain agricultural additives or formulation aids known to those skilled in the art. Such additives or aids may be used to ensure that the plant stress mitigating compound and compositions disperse well in a spray tank, stick to or penetrate plant surfaces (particularly leaf surfaces) as well as provide other benefits to the plant. For example, surfactants, dispersants, humectants, and binders may be used to disperse the plant stress mitigating compound or composition in a spray tank as well as allow the composition or compound to adhere and/or penetrate the plant surfaces. A pesticide may also be included to further protect the plant from pests or disease. The pesticide may be either chemical or biological and includes fungicides, bacteriocides and anti-virals as known in the art. However, since the plant stress mitigating compound increases pesticidal control, it is possible that lower quantities of the pesticide will be needed when the pesticide is combined with the plant stress mitigating compound or compositions of the present invention. In one aspect of the invention, a synergistic composition effective in increasing plant resistance to fungi is provided and includes a fungicide, bacteriocide or antiviral, or a combination thereof, and the compound or compositions described above.

The present invention also provides methods of mitigating plant stress utilizing the compound and compositions described above. In one aspect of the invention, the method involves treating a plant with gamma aminobutyric acid. In another aspect of the invention, the method involves detecting the presence of stress in a plant and treating the plant with gamma aminobutyric acid. Methods of detecting the several types of stress are known in the art.

In another aspect of the invention, the method involves treating a plant with a composition comprising gamma aminobutyric acid in combination with either a source of proteinaceous amino acids (as previously described), or glutamic acid. The composition comprising gamma aminobutyric acid and glutamic acid may further include a source of proteinaceous amino acids.

In other aspects of the invention, the method involves detecting the presence of stress in a plant and treating the plant with gamma aminobutyric acid alone, with glutamic acid or with both glutamic acid and a source of proteinaceous amino acids.

In yet other aspects of the invention, the method involves treating a plant with synergistic composition including a pesticide, gamma aminobutyric acid, glutamic acid and a source of proteinaceous amino acids.

The methods for mitigating plant stress include treating a plant with the compositions described above that further include a calcium salt as described above. Moreover, the compositions may also be combined with a suitable carrier medium as described above.

The present invention also provides methods of preventing plant stress or mitigating the effects of plant stress that include applying the compound or compositions described above at the above-described concentrations and in the above-described amounts prior to the occurrence of plant stress. In one aspect of the invention, the method includes initially predicting when a stressful condition will arrive and then treating the plant prior to arrival of the stressful condition. For example, if severe frost is predicted, the plant may be treated with the compound or compositions of the present invention prior to the cold temperature stress.

As another example, if disease is more likely to occur during certain times of the year, the plants may be treated prior to these times.

The plant stress mitigating compound and compositions of the present invention are typically applied to either the roots or foliage of the plant, and may also be used with seeds.

The methods, compound and compositions of the present invention may be used with recreational or decorative plants or crops but is particularly useful for treating commercial crops. Examples of plants and crops that may be treated in the present invention include monocotyledons, such as duckweed, corn, turf (including rye grass, Bermuda grass, blue grass, fescue), dicotyledons, including cereals such as wheat, crucifers (such as rapeseed, radishes and cabbage), solanaceae (including green peppers, potatoes and tomatoes), and legumes such as soybeans and bush bears.

Reference will now be made to specific examples using the processes described above. It is to be understood that the examples are provided to more completely describe preferred embodiments, and that no limitation to the scope of the invention is intended thereby.

EXAMPLE 1

Effect of GABA on Reducing Nutrient Stress

Bermuda sod was purchased from Oaks Nursery, Knoxville, Tenn. and grown in 4¼" (10.80 cm) diameter black plastic pots containing Fafard #2 potting soil. Two weeks after transfer to pots, turf was cut and each pot given a 50 ml treatment solution. Scotts Liquid Lawn Fertilizer (Fert.) with an N.P.K. of 26:1:2 (0.344 g fert./pot equivalent to 2 lbs. (0.91 kg) N (nitrogen)/1000 sq. ft. (93 sq. m.)) provided treatments with N dressings equivalent to ½ (0.23), 1 (0.45) and 2 (0.91) lbs. (kg) N/1000 sq. ft. (93 sq. m.). For a combination of the invention, one treatment contained fertilizer at ½ lb. (0.23 kg) N and GABA at 5 mM. Each treatment consisted of ten replicate pots. The turf was harvested one week after treatment and the average dry weight of turf was determined. The results in Table 1 show the average dry weight from ten pots for each treatment.

TABLE 1

| Treatment | Average Dry Weight (mg) ± SD* |
|---|---|
| Control-No Treatment | 335 ± 87 |
| Fertilizer ½lb. (0.23 kg) N | 448 ± 107 |
| Fertilizer 2 lb. (0.23 kg) N | 640 ± 229 |
| Fertilizer ½lb. (0.23 kg) N + GABA 5 mM | 644 ± 214 |

*Standard Deviation

Statistical analysis of the data using the student's t-test showed that the weight of turf treated with fertilizer at the equivalent of ½ lb. (0.23 kg) N per 1000 sq. ft. (93 sq. m.) was significantly less (t≧95) than the weight of turf treated with 2 lbs. (0.91 kg) N per 1000 sq. ft. (93 sq. m.) The weight of grass harvested from the treatment given ½ lb. (0.23 kg) N fertilizer+GABA at 5 mM was statistically significantly greater (t≧95) than the weight of grass harvested from the ½ lb. (0.23 kg) N fertilizer treatment without GABA, but was not different from the 2 lb. (0.91 kg) N per 1000 sq. ft. (93 sq. m.) treatments. Results show that the addition of GABA was able to reverse the reduction in plant growth due to lowering nutrient levels from 2 lbs. (0.91 kg) to ½ lb. (0.23 kg) N per 1000 sq. ft. (93 sq. m.).

EXAMPLE 2

Effect of GABA on Reducing Nutrient Stress

Duckweed (Lemma Minor L) was grown according to the general procedure in U.S. Pat. No. 5,439,873. The nutrient media contained different levels of 20-20-20 fertilizer with and without mixtures of casein hydrolysate (1000 ppm) and 10 mM GABA and mixtures of casein hydrolysate and glutamic acid (10 mM). Each treatment consisted of 4 replicate cultures and after two weeks growth, cultures were harvested and dry weights determined. Results are shown in FIG. 1. In fertilizer only treatment, optimal plant growth occurred at 1 g/l fertilizer (18 mgs plant dry weight). When fertilizer levels were reduced to 0.125 g/l, only 5 mg plant growth was found. However, in treatments containing the same level of fertilizer plus casein hydrolysate and GABA, and casein hydrolysate and glutamic acid, plant dry weights were about ten times higher. This shows that the mixtures were able to relieve the nutrient stress caused by limited fertilizer. Similarly, at high levels of fertilizer (4 g/l), duckweed growth was reduced by more than 50% because of an excess of fertilizer. The addition of casein hydrolysate and GABA, or casein hydrolysate and glutamic acid, relieved stress associated with the overabundance of nutrients and plant growth was more than twice that found with the best level of fertilizer. This example shows that treating duckweed with casein hydrolysate in combination with either GABA or glutamic acid, reversed the loss in plant growth due to nutrient excess or nutrient deficiency.

EXAMPLE 3

Effect of AuxiGro™ on Reducing Nutrient Stress

The procedure described in Example 1 was followed except that a fertilizer treatment at 4 lbs. (1.81 kg) N/1000 sq. ft. (93 sq. m.) was included and a composition of 1000 ppm each of GABA, glutamic acid and casein hydrolysate was used in place of pure GABA. The formulated 1:1:1 mixture of GABA, glutamic acid, and casein hydrolysate (GGC) is trademarked "AuxiGro™ WP Plant Metabolic Primer". The dry weight of turf harvested one week after being treated is shown in Table 2 below.

TABLE 2

| Nutrient Treatment | Average Dry Wt. (mg) | % Change from Water Control | % Change From 4 lbs. (1.81 kg) Fertilizer |
|---|---|---|---|
| Tap water | 438 ± 108 | 0 | −39 |
| Fertilizer ½lb. (0.23 kg) | 479 ± 138 | +9 | −34 |
| Fertilizer 1 lb. (0.45 kg.) | 650 ± 254 | +48 | −10 |
| Fertilizer 2 lb. (0.91 kg) | 638 ± 185 | +46 | −12 |
| Fertilizer 4 lb. (1.81 kg) | 720 ± 287 | +64 | 0 |
| Fertilizer ½lb. (0.23 kg) + GABA + Glutamic Acid + Casein Hydrolysate (GGC) | 718 ± 174 | +64 | 0 |

The weight of turf treated with ½ lb. (0.23 kg) fertilizer plus GGC was statistically heavier (≧0.99) than the weight of turf treated with ½ lb. (0.23 kg) fertilizer alone, and very similar to the weight of turf given 8 times more fertilizer. Insufficient nutrients in ½ lb. (0.23 kg) fertilizer limited turf growth in this treatment such that the dry weight of harvested turf was 34% less than the dry weight of turf harvested from the 4 lbs. (1.81 kg) fertilizer treatments.

However, this loss in growth was relieved by treatment with GGC (AuxiGro™).

EXAMPLE 4

Effect of AuxiGro™ on Protecting Plant Tissue From Pathogenic Stress

Potato tubers were surface sterilized and then sliced (laterally) into 1.0 cm thick slices. Tuber slices were treated with a 1:1:1 mixture of gamma aminobutyric acid:glutamic. acid:casein hydrolysate (GGC) at concentrations of either 100, 500, or 1,000 ppm or with water. Slices were challenge inoculated with the potato dry rot pathogen, *Fusarium sambucinum*, by placing an agar plug containing the pathogen onto the surface of the slice. Treated or untreated tuber slices were challenge inoculated with the pathogen either 1, 2, or 3 days after treatment. In all cases, the results were recorded 3 days after the challenge inoculation and included diameter of discoloration (i.e., diameter of visible surface symptoms) and depth of maceration (i.e., range of depth of decay into the tuber tissue) N=6 for each time/treatment.

The results demonstrate that treatment with the combination of GGC protected tissue against the disease pathogen. This is evident by the range of depth of lesions whereby the untreated water controls became completely macerated within 3 days of challenge while those treated with either 100, 500, or 1,000 ppm AuxiGro™ had only surface discoloration and shallow lesions but were typically not macerated by the pathogen. This demonstrates that the use of the GGC combination comprising AuxiGro™ resulted in the plant becoming resistant to the fungal challenge inoculation.

result of infection, the control plants had much poorer seed set and showed very uneven growth. The heads of wheat were harvested and the grain was separated, weighed, and counted. Results are shown in Table 4 for a representative three pots from each treatment.

TABLE 4

| Treatment | Average Grain ± SD* | Average Number of Wheat Grains |
|---|---|---|
| Untreated | 11.75 ± 0.56 | 127 ± 4 |
| AuxiGro ™ ¼lb./ Acre (0.28 kg/hectare) | 15.81 ± 0.56 | 129 ± 4 |

*Standard Deviation

Statistical analysis of the above results show that the 35% increase in grain weight from the AuxiGro™-treated plants was significant at 0.99% confidence.

Tissue samples of control and AuxiGro™-treated wheat plants were analyzed to determine their mineral content. Results are shown below in Table 5.

TABLE 5

Wheat Plant Nutrient Analysis

| | Control | AuxiGro ™ | % of Control |
|---|---|---|---|
| N % | 2.55 | 2.21 | 86.7 |
| P % | 0.817 | 1.16 | 142.0 |
| K % | 3.42 | 4.38 | 128.1 |
| Ca % | 1.1 | 1.44 | 130.9 |

TABLE 3

Time of Challenge Inoculation (Days after Treatment) and Disease Symptoms[1]

| | 1 | | 2 | | 3 | |
|---|---|---|---|---|---|---|
| Treatment | Discoloration | Lesion Depth | Discoloration | Lesion Depth | Discoloration | Lesion Depth |
| Water | 2.56 cm | CM[2] | 3.30 cm | 6–8 mm | 3.87 cm | CM |
| GGC (100 ppm) | 2.25 cm | 5–10 mm | 3.17 cm | SD[3] - 4 mm | 2.95 cm | 2mm-CM |
| GGC (500 ppm) | 2.33 cm | 1–3 mm | 3.30 cm | SD | NT[4] | NT |
| GGC (1000 ppm) | 2.00 cm | SD - 1 mm | 2.70 cm | SD - 6 mm | 2.15 cm | SD - 2 mm |

[1]Symptoms measured as diameter (cm) of discolored tissue and range of depth of lesions (mm) for all 6 replications within each treatment.
[2]CM = Complete maceration of tissue.
[3]SD = Surface discoloration only.
[4]NT = Not tested.

EXAMPLE 5

Effect of AuxiGro™ on Reducing Plant Disease

Wheat seeds cv (Kulm Albert Lea Seed House, Albert-Lea, Minn.) were planted at 100 seeds/1 gallon (3.8 l) pots using SURE MIX potting soil from Michigan Grower Supply, Inc. (Galesburg, Mich.). Control and AuxiGro™ treatments each consisted of three repetitions with 3 pots a repetition, giving a total of 9 pots for each treatment The pots of wheat were treated with AuxiGro™ at ¼ lb/acre (0.28 kg/hectare) a few days before heads could be felt in sheaths of wheat plants. A second AuxiGro™ application was made 3 weeks later by which time flowering had ended and grain set commenced. When applying AuxiGro™, each pot of wheat plants were given 4 sprays equivalent to 10.7 ml per pot.

Plants treated with AuxiGro™ were much more resistant to powdery mildew disease than untreated controls. As a

TABLE 5-continued

Wheat Plant Nutrient Analysis

| | Control | AuxiGro ™ | % of Control |
|---|---|---|---|
| Mg % | 0.672 | 0.844 | 125.6 |
| Na % | 0.017 | 0.023 | 135.3 |
| S % | 0.214 | 0.164 | 76.6 |
| Zn ppm | 77 | 102 | 132.5 |
| Fe ppm | 271 | 233 | 86.0 |
| Mn ppm | 635 | 838 | 132.0 |
| B ppm | 59 | 78 | 132.2 |
| Cu ppm | 8 | 9 | 112.5 |

The results show that AuxiGro™-treated wheat plants had higher levels of minerals, such as manganese, which help plants resist powdery mildew disease.

EXAMPLE 6

Effect of AuxiGro™ on Increasing Activity of Fungicides

The ability of AuxiGro™ to increase plant resistance to fungal attack, thereby increasing effectiveness of fungicides, was demonstrated on tomatoes in Late Blight Control. An entire field of tomatoes which had received two applications of Dithane fungicide as a preventative treatment was showing signs of late blight infection. Plants were large with almost fully-sized fruit when they were treated with Dithane alone and Dithane at the recommended rate in combination with 2 oz/A AuxiGro™. Twenty feet of tomato bed was treated followed by a second application eight days later. A week later, plants were evaluated for severity of late blight infection on a scale of 0–100%, (one spot per leaf=5%, many leaves and main stem infection=50% or more). Results are shown in Table 6.

TABLE 6

| Disease Rating | Dithane | Dithane + AuxiGro ™ |
| --- | --- | --- |
| % plants showing some infection | 57 | 21 |
| % plants showing severe infection | 52.5 | 19 |

The results showed that the addition of AuxiGro™ to the fungicide Dithane increased the effectiveness of Dithane to protect plants from late blight. Fewer than half as many plants became infected after being treated with the mixture of Dithane and AuxiGro™ as became infected following treatments with Dithane alone. The number of plants exhibiting severe signs of infection were also markedly reduced by being treated with the mixture. There is a clear synergy between AuxiGro™ and the fungicide since AuxiGro™ alone has no known activity as a disease protectant agent. However, Dithane and AuxiGro™ is clearly much more effective than Dithane alone.

A second evaluation was performed to compare the effectiveness of Quadris fungicide (Zeneca) and Quadris at the recommended label rate in combination with AuxiGro™ at 2 oz/acre (0.14 g/hectare). The procedure described with Dithane fungicide was followed except that only a single application of Quadris and Quadris in combination with AuxiGro™ was made to large plants with almost fully sized fruit (Oct. 28, 1997). Plants were evaluated for disease at harvest (Nov. 11, 1997), using the same measurements of infection described in the previous example. Results are shown in Table 7.

TABLE 7

| Disease Rating | Quadris | Quadris + AuxiGro ™ |
| --- | --- | --- |
| % of plants showing some infection | 19.5 | 6.9 |
| % plants showing severe infection | 13.3 | 6.9 |

Results show that the addition of AuxiGro™ to the fungicide Quadris increased the effectiveness of the fungicide. Fewer than half as many plants showed signs of late blight infection when treated with the mixture of fungicide and AuxiGro™ compared to plants treated with the fungicide alone. This provides a further example of synergy between AuxiGro™ and the fungicide Quandris.

Although not being limited by theory, the benefits of AuxiGro™ treatments in Example 6 are believed to result either from the increase in plant resistance to disease demonstrated in Examples 4 and 5, or by enhanced metabolism of the fungicide by the fungal pathogen and hence increased pesticidal activity. By increasing plant resistance to the fungal infection, less fungicide is needed to protect plants.

EXAMPLE 7

Effect of AuxiGro™ on Protecting Plants From Copper Salt Stress

The experiment was designed to determine the effect of AuxiGro™ on plant toxicity caused by excessive amounts of copper salts. Duckweed was grown following the procedure described in Example 1. A control sample of duckweed was treated with 1 g/l 20-20-20 fertilizer and other samples were treated with copper salts or a combination of copper salts and 1,000 ppm AuxiGro™. After fifteen days of growth, cultures were harvested and dry weights determined. Results are shown in Table 8.

TABLE 8

| Treatment | Average Dry Weight (mg) ± SD† | % Change From Control |
| --- | --- | --- |
| Control | 27.7 ± 2.9 | 0 |
| Copper* 3.3 ppm | 8.3 ± 0.7 | −70 |
| Copper 3.3 ppm + AuxiGro ™ 1,000 ppm | 20.1 ± 1.5* | −27 |
| Copper 1.7 ppm | 18.0 ± 4.7 | −35 |
| Copper 1.7 ppm + AuxiGro ™ 1,000 ppm | 83.5 ± 5.8 | +201 |
| AuxiGro ™ 1,000 ppm | 86.6 ± 9.1 | +213 |

*Copper was provided from $CuSo_4 5H_2O$
†Standard Deviation

Results show that AuxiGro™ relieved the growth inhibition caused by copper toxicity. Copper at 1.7 ppm reduced duckweed growth by 35%. However, plant growth increased more than two-fold in the sample treated with the same level of copper and 1,000 ppm AuxiGro™ compared to control medium without copper salts.

EXAMPLE 8

Effect of AuxiGro™ on Protecting Plants From Toxic Effects of Aluminum Salts The procedure described in Example 7 was followed except that aluminum chloride at 5 mM equivalent to 134 ppm $Al^{3+}$ was used as the test salt with and without 1,000 ppm AuxiGro™. After nineteen days growth, the cultures were harvested and dry weights determined. Results are shown in Table 9.

TABLE 9

| Treatment | Average Dry Weight (mg) ± SD* | % Change Over Control |
| --- | --- | --- |
| Control Table 9 | 67.6 ± 7.3 | 100 |
| $AlCl_3$ 5 mM | 53.2 ± 5.4 | −21 |
| $AlCl_3$ 5 mM AuxiGro ™ 1000 ppm | 78.2 ± 6.1 | +116 |

*Standard Deviation

Results show that duckweed growth was reduced by more than 20% as shown by the decrease in dry weight when 5 mM aluminum chloride was added to culture media. AuxiGro™ at 1000 ppm more than relieved the growth reduction cause by aluminum and average plant growth in media containing a mixture of aluminum and AuxiGro™ was higher than in control medium.

EXAMPLE 9

Effect of AuxiGro™ in Relieving Growth Reduction Due to Cold Treatment

Figure 2:
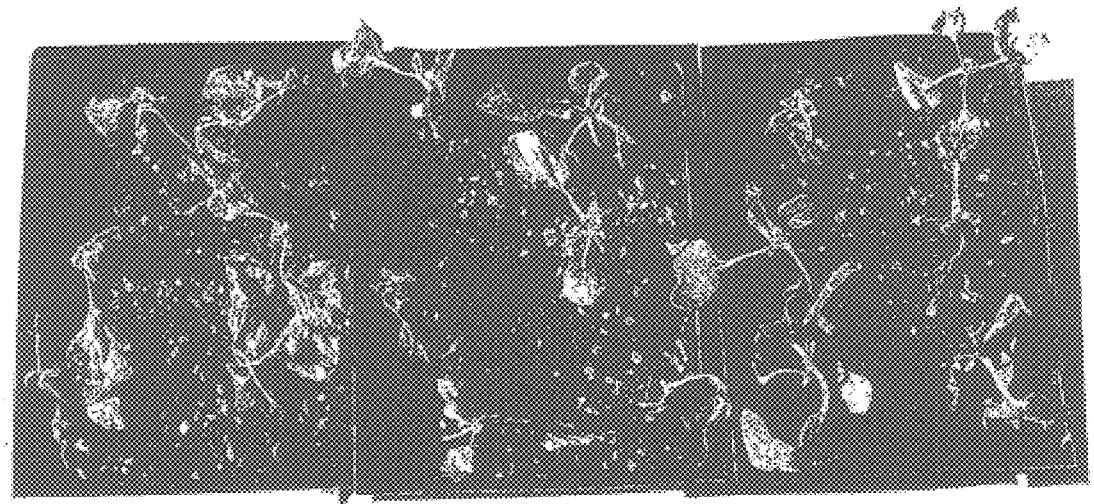
FIG. 2 depicts the effect of AuxiGro™ in relieving growth reduction of cabbage plants due to cold treatment. Top left panel: control; top middle panel: plants treated with 150 ppm AuxiGro™ containing yeast extract in place of casein hydrolysate (AuxF05); top right panel: slants treated with 150 ppm AuxF05 and 5,000 ppm calcium nitrate. The bottom left and right panels represent the same plants as depicted in the top left and top right panel, respectively, that are in closer proximity to each other so a more direct comparison can be made.
Figure 2:
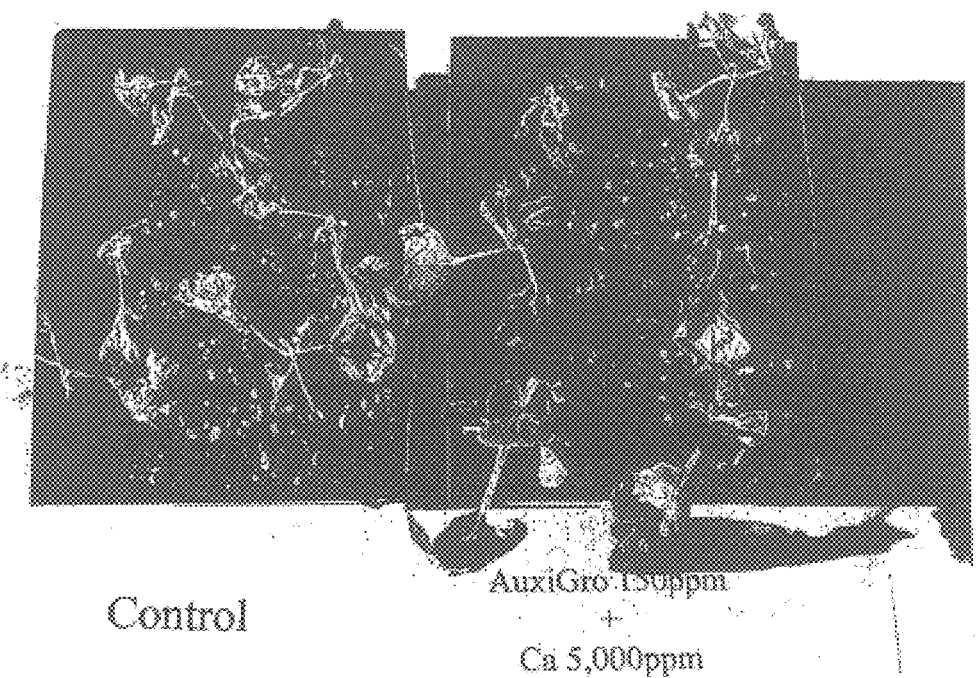

Seeds of Heads Up cabbage were obtained from Harris Seeds, Rochester, N.Y. and grown in 7"×5¼"×2¼" (17.78 cm×13.34 cm×5.72 cm) Kord inserts (Park Seeds, Greenwood, S.C.) containing Bacto potting soil (Michigan Peat Company, Houston, Tex.). After plants had germinated, cabbage seedlings were thinned to six plants per insert. Inserts were kept in 12"×8¾" (30.48 cm×22.23 cm) perma nest trays (Park Seed) with two inserts per tray. Each treatment consisted of three replicate trays containing a total of eighteen cabbage plants. After two weeks, some of the plants were sprayed with AuxiGro™ containing yeast extract in place of casein hydrolysate (AuxF05) and half of all plants subjected to low temperature stress. Storage in a freezer for two hours and forty minutes resulted in total destruction of control plants although some of the AuxiGro™ treated plants survived this treatment (see FIG. 2). When plants were exposed to 1½ hours storage at freezing temperature three times every other day for a total of nine days, the non-lethal exposure inhibited growth by about 10% as shown in Table 10. Plants treated with AuxiGro™ and with AuxF05 combined with calcium nitrate were much less inhibited and the average fresh weights were higher than that of non-treated control plants.

TABLE 10

| Treatment | Mean Fresh Weight (g) ± SD | % Change From Room Temp. Control | % Change From Freeze Control |
|---|---|---|---|
| Control room temp. | 33.8 ± 3.5 | 0 | +10 |
| Control Freezer | 30.6 ± 2.8 | −10 | 0 |
| AuxF05 | 32.8 ± 2.4 | −3 | +7 |
| AuxF05 150 ppm + CaNO₃ 1,000 ppm | 3.3.4 ± 3.0 | −1 | +9 |
| AuxF05 150 ppm + CaNO₃ 2,500 ppm | 35.6 ± 3.7 | +5 | +16 |

AuxF05 = AuxiGro ™ containing yeast extract in place of casein hydrolysate.

Results in Table 10 show that treating plants with AuxF05, AuxiGro™ containing a yeast extract in place of casein hydrolysate, relieves some of the growth decrease due to exposure to freezing temperatures. When calcium nitrate was added to the AuxF05, the freezing-induced decrease in growth was completely relieved. The average weight of cabbage plants treated with the AuxF05 formulation in combination with 2,500 ppm calcium nitrate was 5% higher than the average weight of control plants maintained at room temperature.

EXAMPLE 10

Effect of AuxiGro™ in Relieving Growth Reduction Due to Cold Treatment

Seeds of Annie Oakley II Hybrid Okra were purchased from Park Seed of Greenwood, South Carolina. Seeds were germinated in 4" (10.16 cm) pots filled with Bacto potting mix (Michigan Peat Company, Houston, Tex.). Growing plants were fertilized twice with Peters 20-20-20 fertilizer and twice with 1-50-10 Peters Super Blossom Booster Fertilizer. Plants were treated with AuxiGro™ formulation at the time of fruit set and a second treatment was made seven days later. Some of the plants were given a low temperature treatment (12 hours at 15° C. for five nights) starting the day that the first AuxiGro™ treatment was given.

Okra fruit was harvested from plants following the second treatment when the fruit was at least 4½" (11.43 cm) long. Table 11 shows the percent change in the number and weight of fruit harvested from plants of each treatment compared to the control plants.

TABLE 11

| | Room Temperature | | Low Temperature | |
|---|---|---|---|---|
| Treatment | Avg. Fruit Wt. (g) | % of Control | Avg. Fruit Wt. (g) | % of Room Temperature Control |
| Control | 106 | 100 | 75 | 71 |
| AuxiGro ™ 150 ppm | 126 | 119 | 110 | 104 |
| AuxiGro ™ 300 ppm | 97 | 92 | 105 | 99 |
| AuxiGro ™ 150 ppm + CaNO₃ 5000 ppm | 126 | 119 | 114 | 107 |
| AuxiGro ™ 300 ppm + CaNO₃ 5000 ppm | 108 | 102 | 126 | 119 |

Results from the Okra experiments show that plants subjected to five nights of low temperature treatment yielded 29% less fruit than plants maintained at room temperature. Average fruit weight was increased by 119% when plants were treated with 300 ppm AuxiGro™ in combination with 5000 ppm CaNO₃. Productivity of these plants exceeded that of control plants, notwithstanding the cold treatments. The example shows that treating plants with AuxiGro™ in combination with CaNO₃ is able to relieve loss of productivity due to cold stress. Further, this example shows that AuxiGro™ in combination with calcium nitrate was more effective than AuxiGro™ alone.

EXAMPLE 11

Effect of AuxiGro™ on Relieving Cold-Induced Inhibition of Cotton Seed Germination

Roundup Ready cotton seeds were planted in three rows, with five seeds/row in 7"×5¼" 2¼" (17.78 cm×13.34 cm×5.72 cm) Kord inserts (Park Seed, Greenwood, S.C.) with Bacto potting soil (Michigan Peat Company, Houston, Tex.). Experimental design was intended to simulate "in-furrow" planting of cotton in the field. Each "furrow" (row) was treated with 2 ml of the different compositions equivalent to about 1 oz product/Acre (70 g/hectare). Each treatment consisted of 3 replicate inserts so that each treatment had 45 cotton seeds. Treatments were grown at 75° F. (24° C.) in an incubator with 16 hour days at 59° F. (15° C.) and 8 hour nights at 50° F. (10° C.). The number of cotton seeds germinated in each treatment group was recorded as a function of time and results are shown below in Table 12. None of the control seeds had germinated at 75° F. (24° C.) five days after planting. However, some germination occurred when cotton seeds were treated with AuxiGro™, CaNO₃ and mixtures of AuxiGro™ and CaNO₃. When the seeds were grown at low temperatures, no seeds had germinated in controls 9 days after planting. When seeds were treated with AuxiGro™ alone, 7 seeds (16% of all seeds) germinated, whereas only 6 seeds (13% of all seeds) germinated when seeds were treated with only $CaNO_3$. Increased germination of seeds treated with the mixture of the two components, 21 seeds (47% of all seeds) was higher than that expected from the sum of the individual components. The increased germination observed in seeds treated with AuxiGro™ and mixtures of AuxiGro™ and $CaNO_3$ was still evident 17 days after planting when seedlings were harvested. At this time, the growth of the seeds treated with AuxiGro™ and AuxiGro™ in combination with $CaNO_3$ were 17% and 36%, respectively, greater than controls as determined by seedling weights.

TABLE 12

| Days After Planting | Untreated Control | AuxiGro ™ 300 ppm | $CaNo_3$ 300 ppm | AuxiGro ™ 300 ppm + $CaNO_3$ 300 ppm |
|---|---|---|---|---|
| 5 | 0 a | 4 | 9 | 5 |
|   | 0 b | 0 | 0 |   |
| 7 | 31 a | 27 | 38 | 26 |
|   | 0 b | 0 | 0 | 3 |
| 9 | 36 a | 32 | 41 | 31 |
|   | 0 b | 7 | 6 | 21 |
| 13 | 41 a | 37 | 42 | 34 |
|   | 26 b | 28 | 23 | 37 |
| 17 | 41 a | 39 | 43 | 34 |
|   | 32 b | 36 | 31 | 40 |
| Fresh Wt. (g) | 6.88 a | 6.05 | 8.70 | 5.66 |
|   | 4.15 b | 4.85 | 4.01 | 5.64 | a = 75° F. (24° C.)
b = 59° F. (15° C.)/50° F. (10° C.)

EXAMPLE 12

Effect of AuxiGro™ in Protecting Cabbage From Heat Stress

Plants typically die when exposed to temperatures of 44–50° C. (pp. 487 in: Plant Physiology by F. B. Salisbury and C. W. Ross, Wadsworth Publishing Company). The value of AuxiGro™ in protecting plants from heat stress was demonstrated with cabbage plants following the general procedure described in Example 9. Plants were given two foliar applications of the AuxiGro™ formulations at two weeks and three weeks after seeds were germinated. Three days following the second treatment, plants were placed in an oven at 48° C. (118° F.) for twelve hours. Plants were harvested and weighed one week following the temperature treatment. Results are shown in Table 13.

TABLE 13

| Treatment | Mean Fresh Weight (g) ± SD | % of Room Temperature Control |
|---|---|---|
| Control Room Temperature | 37.2 ± 3.3 | 100 |
| Control Oven | 22.4 ± 1.5 | 60 |
| AuxF05 300 ppm | 34.4 ± 2.9 | 92 |
| AuxF05 300 ppm + $CaNO_3$ 2500 ppm | 37.3 ± 2.1 | 100 |
| $CaNO_3$ 2500 ppm | 28.8 ± 5.6 | 77 |

Results show that heat treatment depressed cabbage growth by 40%. Treating plants with AuxiGro™ relieved the heat-induced growth reduction. Treating plants with AuxiGro™ in combination with $CaNo_3$ completely relieved the negative effects of heat stress. However, treating plants with the same amount of $CaNO_3$ alone only partially relieved the negative effects of heat stress.

EXAMPLE 13

Effect of AuxiGro™ on Relieving Drought Stress

A field test on corn was conducted by Vanguard Agricultural Services Inc. on a field of loam soil near Brighton, Ill. Corn was planted on May 17 and rainfall from May through July was only 4.17 inches (10.60 cm) or 63% less than the average rainfall of 11.4 inches (29 cm) recorded for May–July periods from 1987–1996. As the Nov. 10, 1997 report from Vanguard states "Rains in late August were too late to reverse stress damage and corn yields were significantly reduced vs. the historical average at this location." Table 14 shows the corn yield from the treatments harvested in October.

TABLE 14

| Treatment | Yield (l/ha) | % Change from Control |
|---|---|---|
| Control | 8504 | 0 |
| AuxiGro ™ (0.31 kg/ha) | 9574 | +13 |
| AuxiGro ™ (0.95 kg/ha) | 9374 | +9 |
| AuxiGro ™ (1.90 kg/ha) | 9592 | +13 |

The results show that the yield of corn treated with AuxiGro™ was higher than controls. This demonstrates that AuxiGro™ was able to relive the yield-depressing effects of drought stress.

EXAMPLE 14

Effect of AuxiGro™ on Relieving Other Stresses

Other stresses that increase GABA production in plants will also be relieved by treating plants with AuxiGro™. These stresses, and. examples of the plants affected, are shown in Table 15. Treating the plants with AuxiGro™ will be sufficient to relieve the forms of stress listed in Table 15.

TABLE 15

Kinetics of Stress Induced GABA Accumulation in Plant Tissue

| Plant | Stress | % GABA Increase | Time | Reference |
|---|---|---|---|---|
| Asparagus Cells | Acidification | 300 | 15 sec. | Crawford et al., 1994 |
| Soybeans | Mechanical Damage | 1,000 | 30 sec. | Ramputh and Brown, 1996 |
| Soybeans | Cold Shock | 2,360 | 5 min. | Wallace et al., 1994 |
| Cowpea Cells | Heat Shock | 6,400 | 2 hrs. | Mayer et al., 1990 |
| Tea Leaves | Anaerobosis | 4,000 | 3 hrs. | Tsushida and Murai, 1987 |
| Tomato | Salt Stress | 300 | 4 days | Bolarin et al., 1995 |
| Tomato | Viral Attack | 140 | 3 days | Cooper and Selman, 1974 |
| Cotton | Water Stress | 700 | 24 hrs. | Hanower and Brzozowska, 1975 |

EXAMPLE 15

Effect of a Composition Including Gamma Aminobutyric Acid and Glutamic Acid in Relieving Plants from Stress Compositions including gamma aminobuyric acid and glutamic acid can be used to mitigate plant stress in the absence of a protein hydrolysate or yeast extract. Plants can be treated as described in Examples 1–14 with the gamma aminobutyric acid/glutamic acid composition. The concentrations of each component in the composition can include about 1 ppm to about 8,000 ppm (about 0.013 oz/A to about 6.7 lbs/A) (about 0.93 g/ha to about 7.5 kg/ha), about 1 ppm to about 7,500 ppm (0.013 oz/A to about 6.3 lbs/A) (about 0.93 g/ha to about 7.1 kg/ha) and about 1 ppm to about 5,000 ppm (about 0.013 oz/A to about 4.2 lbs/A) (about 0.93 g/ha to about 4.8 kg/ha). The composition is useful for mitigating the various forms of stress described in Examples 1–14 including nutrient stress, pathogenic stress, and protecting plants from the toxic effects of metal salts, and from adverse environmental stresses.

While the invention has been illustrated and described in detail in the foregoing description, the same is to be considered as illustrative and not restrictive in character, it being understood that only the preferred embodiments have been shown and described, and that all changes and modifications that come within the spirit of the invention are desired to be protected.

What is claimed is:

1. A method of mitigating the effects of plant stress comprising treating the plant with an amount of gamma aminobutyric acid effective in mitigating plant stress, said plant selected from the group consisting of cereals, crucifers, turf, duckweed, corn, and cabbage.

2. The method of claim 1, wherein said gamma aminobutyric acid is combined with a carrier medium.

3. The method of claim 2, wherein said carrier medium is aqueous or solid.

4. The method of claim 1, wherein the plant is treated with about 1 ppm to about 2,500 ppm of gamma aminobutyric acid.

5. The method of claim 1, wherein said plant is treated with a composition comprising gamma aminobutyric acid and a source of proteinaceous amino acids.

6. The method of claim 1, wherein said plant is treated with a composition comprising gamma aminobutyric acid and glutamic acid.

7. The method of claim 5, wherein said composition further includes a source of proteinaceous amino acids.

8. The method of claim 7, wherein said composition is in a carrier medium.

9. The method of claim 1, wherein said plant is treated with about 150 ppm to about 600 ppm gamma aminobutyric acid.

10. The method of claim 1, wherein said gamma aminobutyric acid is applied to the seeds of said plant.

11. A method of mitigating the effects of plant stress comprising:

detecting the presence of stress in a plant; and treating the plant with gamma aminobutyric acid, said plant selected from the group consisting of cereals, crucifers, turf, duckweed, corn, and cabbage.

12. The method of claim 11, wherein said gamma aminobutyric acid is combined with a carrier medium.

13. The method of claim 11, wherein said plant is treated with a composition comprising gamma aminobutyric acid and a source of proteinaceous amino acids.

14. The method of claim 11, wherein said plant is treated with a composition comprising gamma aminobutyric acid and glutamic acid.

15. The method of claim 14, wherein said composition further includes a source of proteinaceous amino acids.

16. The method of claim 15, wherein said gamma aminobutyric acid is present in a concentration of about 1 ppm to about 2,500 ppm, said glutamic acid is present in a concentration of about 1 ppm to about 2,500 ppm, and said source of proteinaceous amino acids is present in a concentration of about 1 ppm to about 2,500 ppm.

17. The method of claim 15, wherein said source of proteinaceous amino acids is a protein hydrolysate.

18. The method of claim 17, wherein said protein hydrolysate is casein hydrolysate.

19. The method of claim 15, wherein said source of proteinaceous amino acids is a yeast extract.

20. The method of claim 15, wherein said composition further includes a salt of calcium.

21. The method of claim 20, wherein said salt of calcium is calcium nitrate.

22. The method of claim 20, wherein said salt of calcium is present in a concentration of about 100 ppm to about 10,000 ppm.

23. The method of claim 15, wherein the plant is treated with said composition comprising gamma aminobutyric acid, said glutamic acid and said source of proteinaceous amino acids in an amount effective in mitigating plant stress.

24. The method of claim 15, wherein said composition is applied to the foliage of said plant.

25. The method of claim 15, wherein said composition is applied to the roots or seeds of said plant.

26. A method of preventing plant stress comprising treating the plant with gamma aminobutyric acid prior to the occurrence of plant stress, said plant selected from the group consisting of cereals, crucifers, turf, duckweed, corn, and cabbage.

27. The method of claim 26, wherein said plant is treated with a composition comprising gamma aminobutyric acid and glutamic acid.

28. The method of claim 27, said composition further comprising a source of proteinaceous amino acids.

29. The method of claim 28, said composition further comprising a salt of calcium.

30. A method of mitigating the effects of plant stress, comprising:

a) predicting when a stressful condition will arrive; and b) treating the plant with gamma aminobutyric acid prior to the occurrence of plant stress, said plant selected from the group consisting of cereals, crucifers, turf, duckweed, corn, and cabbage.

31. The method of claim 30, wherein said plant is treated with a composition comprising gamma aminobutyric acid and glutamic acid.

32. The method of claim 31, said composition further comprising a source of proteinaceous amino acids.

33. A plant stress mitigating composition comprising gamma aminobutyric acid and a source of proteinaceous amino acids.

34. The plant stress mitigating composition of claim 33, wherein said gamma aminobutyric acid and said source of proteinaceous amino acids are combined with a carrier medium.

35. The method of claim 33, wherein said source of proteinaceous amino acids is a protein hydrolysate.

36. The method of claim 35, wherein said protein hydrolysate is selected from the group consisting of yeast extract and casein hydrolysate.

37. A method of mitigating the effects of plant stress comprising treating the plant with an amount of a composition comprising gamma aminobutyric acid and a source of proteinaceous amino acids effective in mitigating plant stress.

38. The method of claim 37, wherein said source of proteinaceous amino acids is a protein hydrolysate.

39. The method of claim 38, wherein said protein hydrolysate is selected from yeast extract and casein hydrolysate.

40. A plant stress mitigating composition comprising glutamic acid and a source of proteinaceous amino acids.

41. The plant stress mitigating composition of claim 40, wherein said glutamic acid and said source of proteinaceous amino acids are combined with a carrier medium.

42. A method of mitigating the effects of plant stress comprising treating the plant with a composition comprising glutamic acid and a source of proteinaceous amino acids.

43. The method of claim 42, wherein said glutamic acid and said source of proteinaceous amino acids are combined with a carrier medium.

44. A method of mitigating the effects of plant stress comprising:

detecting the presence of stress in a plant; and treating the plant with a composition comprising glutamic acid and a source of proteinaceous amino acids.

45. The method of claim 44, wherein said glutamic acid and said source of proteinaceous amino acids are combined with a carrier medium.

46. A plant stress mitigating composition comprising gamma aminobutyric acid and glutamic acid.

47. The plant stress mitigating composition of claim 37, further comprising a source of proteinaceous amino acids.

48. The plant stress mitigating composition of claim 47, wherein said gamma aminobutyric acid, said glutamic acid and said source of proteinaceous amino acids are present in combined amounts effective in mitigating plant stress.

49. The plant stress mitigating composition of claim 48, wherein said gamma aminobutyric acid is present in a concentration of about 1 ppm to about 5,000 ppm, said glutamic acid is present in a concentration of about 1 ppm to about 5,000 ppm and said source of proteinaceous amino acids is present in a concentration of about 1 ppm to about 5,000 ppm.

50. The plant stress mitigating composition of claim 47, wherein said source of proteinaceous amino acids is a protein hydrolysate.

51. The plant stress mitigating composition of claim 50, wherein said protein hydrolysate is casein hydrolysate.

52. The plant stress mitigating composition of claim 47, wherein said source of proteinaceous amino acids is a yeast extract.

53. The plant stress mitigating composition of claim 47, wherein said composition further includes a calcium salt.

54. The plant stress mitigating composition of claim 53, wherein said calcium salt is present in a concentration of about 100 ppm to about 10,000 ppm.

55. The plant stress mitigating composition of claim 53, wherein said salt of calcium is calcium nitrate.

56. A method of mitigating the effects of plant stress comprising treating the plant with an amount of a composition comprising gamma aminobutyric acid and glutamic acid effective in mitigating plant stress.

57. The method of claim 56, wherein said composition further includes a source of proteinaceous amino acids.

58. The method of claim 57, wherein said source of proteinaceous amino acids is a protein hydrolysate.

59. The method of claim 58, wherein said protein hydrolysate is selected from yeast extract and casein hydrolysate.

60. The method of claim 57, wherein said composition further includes a calcium salt.

61. The method of claim 60, wherein said calcium salt is calcium nitrate.

62. A synergistic composition effective in increasing the level of control of plant pathogens comprising a pesticide, gamma aminobutyric acid, glutamic acid and a source of proteinaceous amino acids.

63. The composition of claim 62, wherein said pesticide is a fungicide.

64. The composition of claim 62, wherein said pesticide is a bacteriocide.

65. The composition of claim 62, wherein said pesticide is an anti-viral.

66. The composition of claim 62, wherein said pathogen is selected from the group consisting of fungi, bacteria and viruses.

67. The composition of claim 62, wherein said composition further includes a calcium salt.

* * * * *